(12) United States Patent
Steffen (10) Patent No.: US 10,010,344 B2
(45) Date of Patent: Jul. 3, 2018

(54) SELF-DILATING CATHETER INTRODUCER WITH OBTURATOR AND METHOD OF USE

(71) Applicant: Dennis L Steffen, Tavernier, FL (US)

(72) Inventor: Dennis L Steffen, Tavernier, FL (US)

( * ) Notice: Subject to any disclaimer, the term of this patent is extended or adjusted under 35 U.S.C. 154(b) by 483 days.

(21) Appl. No.: 14/798,383

(22) Filed: Jul. 13, 2015

(65) Prior Publication Data

US 2017/0014156 A1    Jan. 19, 2017

(51) Int. Cl.
*A61B 17/34* (2006.01)
*A61M 25/06* (2006.01)
*A61M 25/00* (2006.01)

(52) U.S. Cl.
CPC ..... *A61B 17/3439* (2013.01); *A61M 25/0023* (2013.01); *A61M 25/0662* (2013.01); *A61M 2025/0024* (2013.01); *A61M 2025/0681* (2013.01)

(58) Field of Classification Search
CPC .......... A61M 25/0032; A61M 25/0023; A61M 2025/0681; A61M 2025/0004; A61B 17/3439
See application file for complete search history.

(56) References Cited

U.S. PATENT DOCUMENTS

| | | | | |
|---|---|---|---|---|
| 3,788,318 A * | 1/1974 | Kim | .................. | A61M 5/00 604/104 |
| 3,789,852 A * | 2/1974 | Kim | .................. | A61B 17/3439 604/104 |
| 4,451,256 A * | 5/1984 | Weikl | ................ | A61M 25/0668 604/164.03 |
| 4,946,443 A | 8/1990 | Hauser | | |
| 5,066,285 A | 11/1991 | Hillstead | | |
| 5,183,464 A * | 2/1993 | Dubrul | .............. | A61M 25/0023 604/104 |
| 5,423,762 A | 6/1995 | Hillstead | | |
| 5,466,230 A | 11/1995 | Davila | | |
| 5,628,732 A | 5/1997 | Antoon, Jr. | | |
| 5,782,817 A | 7/1998 | Franzel | | |
| 5,882,345 A * | 3/1999 | Yoon | .................. | A61B 17/3439 604/104 |
| 5,897,497 A | 4/1999 | Fernandez | | |
| 5,908,435 A * | 6/1999 | Samuels | .......... | A61B 17/22031 606/127 |
| 5,961,499 A * | 10/1999 | Bonutti | .............. | A61B 17/0401 604/164.11 |
| 6,190,357 B1 * | 2/2001 | Ferrari | ............... | A61B 17/3439 604/102.01 |
| 6,989,003 B2 | 1/2006 | Wing | | |
| 7,172,027 B2 | 2/2007 | Simpson | | |
| 7,449,011 B2 * | 11/2008 | Wenchell | ........... | A61B 17/3421 604/104 |
| 7,637,902 B2 * | 12/2009 | Eversull | ........... | A61M 25/0668 604/524 |
| 7,927,309 B2 | 4/2011 | Palm | | |

(Continued)

*Primary Examiner* — Matthew F DeSanto (57) ABSTRACT

The present invention relates generally to medical devices and, in particular, to a self-dilating catheter introducer and obturator system for introducing implantable medical devices into a body cavity. Depending on the size of the orifice or opening in which the device is required to pass through determines the French scale size of the device (e.g. The French scale is a measure of the external diameter of a catheter not internal channel).

10 Claims, 10 Drawing Sheets

SECTION 3-3

(56) References Cited

U.S. PATENT DOCUMENTS

| | | | | |
|---|---|---|---|---|
| 8,597,277 B2* | 12/2013 | Lenker | ............... | A61B 17/3439 |
| | | | | 264/301 |
| 9,168,359 B2* | 10/2015 | Rowe | ................ | A61M 25/0014 |
| 2001/0001813 A1* | 5/2001 | West | ................ | A61M 39/0606 |
| | | | | 604/256 |
| 2015/0073333 A1* | 3/2015 | Knowles | ............ | A61B 17/3439 |
| | | | | 604/26 |
| 2015/0265802 A1* | 9/2015 | Fukuoka | ........... | A61M 25/0021 |
| | | | | 604/508 |

* cited by examiner

FIG. 1

SECTION 2-2　　FIG. 2

DETAIL 4

FIG. 3

SECTION 3-3

SELF-DILATING CATHETER INTRODUCER WITH OBTURATOR AND METHOD OF USE

CROSS REFERENCES TO RELATED APPLICATIONS

This application claims the benefit under 35 U.S.C. § 119(e) of U.S. Non-Provisional Application N/A.

FIELD OF THE INVENTION

The present invention relates to a Self-Dilating Catheter Introducer and Obturator. Introducers are used for placing medical devices, including catheters, into a patient. This specification details an introducer that greatly minimizes the need to exchange introducers during a medical procedure with the focus on reducing Vascular Access Site Complications "VASC".

INTRODUCTION

Implants may be placed in the human body for a variety of reasons. For example, stents are placed in a number of different body lumens such as blood vessels and biliary ducts; vena cava filters are implanted in the vena cava to catch thrombus sloughed off from other sites within the body; and vaso-occlusive devices are used for the treatment of intravascular aneurysms. Interventional practitioners, regardless of subspecialty have always had to demonstrate profound dexterity in order to effectively and accurately perform invasive procedures. This is particularly the case with the delivery and deployment of implantable devices where there is very little room for error with respect to placement. In some medical procedures, tubular structures such as sheath introducers are inserted into tissue to allow access to a particular body structure, and medical devices are then passed through the tubular structure to a desired site. A guiding catheter is often passed through an introducer to place the catheter into the vasculature of a patient as a common practice in a catheter based medical procedure. A common scenario where the physician first perform a diagnostic procedure using a relatively smaller French scale e.g. 5F diagnostic device requiring a smaller French scale introducer e.g. 5F. Then in order to insert the interventional device required to complete the procedure e.g. stent delivery device, the physician may need to replace the smaller French scale introducer with one of larger French scale e.g. 8F that will allow the passage of the interventional device, resulting in an increase of procedural time and revision that may increase complications. Relative to the current most common method the single most frequent cause of complications during coronary angioplasty and interventions are those related to Femoral Access Interventions "Incidence and results of arterial complications among 16,350 patients undergoing cardiac catheterization; Journal of Vascular Surgery". With Manual Compression is the most common form of closure globally for Femoral Access Interventions historical advice on bedrest with sheath and introducer size dependent with the corresponding leg straight for a minimum of 1 Hour for each French size of the arterial sheath. (e.g. 10F=10 hours). Ambulation post sheath removal for 5Fr Sheath is approximately 1 Hour "Ambulation 1 hour after diagnostic cardiac catheterization, a prospective study of 1009 patients; Mayo Clinic, 2006". In many institutions manual compression is associated with the lowest VASC rates and instrument related procedural cost. Relative a newer more progressive approach the Transradial Access Interventions continues to rise even replacing femoral access as the preferred choice in some countries. Globally Transradial Access Intervention is utilized in 20% of the total cases for PCI, 29% when excluding the US market, Norway, Malaysia, and Bulgaria have the highest rates in excess of 70% while Central and South America at an estimated 15% rate. As the evolution of PCI's have progressed to incorporate targeted anticoagulants and antiplatelet agents that have led to a steady decrease in ischemic complication there has been a renewed focus on nonischemic complications especially VASCs and ambulation time associated with increased patient stay and cost which has driven a large focus to the Transradial Approach. Transradial access is the preferred choice for upper extremity access because of its easy compressibility, distance from major veins and nerves, companion blood flow through the ulnar artery to the palmar arch. Use of Radial Artery for diagnostic and interventional procedures has been compared with femoral and brachial approach in both randomized trials and observational studies, and has consistently demonstrated statistically significant reductions in bleeding and access site complications. The improvements are even more pronounced in women who have a 2-3 times higher risk of femoral access complications compared to men. Reduced complications lead to reduced lengths of stay and reduced procedural cost and improved clinical outcomes. Although femoral devices have also improved early ambulation and reduced patient discomfort, they have not demonstrated a reduction in bleeding and VASCs. Transradial access compared with femoral puncture closure devices in percutaneous coronary procedures "International Journal of Cardiology, 2009". There is a significant difference in VASC's related to Transradial approach using 5F verse 6F introducers. Routine vascular ultrasound after radial artery cauterization detects clinically silent access site complications: "Prospective registry of 425 consecutive patients; University of Leipzig, Herzzentrum".

In summary VASC's (Vascular Access Site Complications): VASC's are defined as vascular complications such as pseudoanneuryism, ateriovenus fistula, femoral neuropathy, retroperitoneal hematoma, any complication requiring surgical repair, and hematoma requiring transfusion, prolonged hospital stay, or causing a drop in Hgb>3.0 g/dl. This does not include excessive closure time associated with standard closure techniques, impact on the location of femoral access, or number of attempts to gain access, reported incidence of VASC's is 5.4 to 20%, procedure Cost for PCI when bleeding complications arouse can result in more than double that of uncomplicated cases. Managing the risk of complications at a femoral access site in percutaneous coronary interventions; "Critical Care Nurse Vol. 32, No. 5, 2012" complications are related to a number of factors: Patent, Procedure, Operator, Institutional, and other related variables. Vascular access site complications are more common in larger access devices regardless if closure devices are being utilized. The data from this study suggest that the use of smaller guiding/introducer catheters during PCI is associated with significantly better outcome, including improved post procedural morbidity and reduced mortality. Percutaneous Coronary Interventions Complications & Guide Catheter Size "Bigger is not Better"; JACC Vol. 2, No. 7, 2009. It has long been documented that the larger the access site introducer/guide catheter the higher the rate of complications especially in VASC's (Vascular Access Site Complications).

Percutaneous Coronary Interventions Complications & Guide Catheter Size "Bigger is not Better"; *JACC* Vol. 2, No. 7, 2009

Managing Risk of Complications at Femoral Access Sites in Percutaneous Coronary interventions; *Critical Core Nurse* Vol. 32, No. 5, 2012

Economic Burden of Complications During Percutaneous Coronary Interventions; *Qual Saf Healthcare,* 2007

Major Femoral Bleeding Complications After Percutaneous Coronary Interventions: incidence, Predictors, and Impact on Long Term Survival; *JACC,* Vol. 1, No. 2, 2008

Peripheral Vascular Complications Following Coronary Percutaneous Interventional Procedures; *Clinical Cardiology,* 1995

Hospital Resources Consumed in Treating Complications Associated with Percutaneous Coronary Interventions; *American Journal or Cardiology,* 2006

Risk Factors for the Development of Retroperitoneal Hematoma after Percutaneous Coronary Interventions: *Journal of American College,* 2005

Femoral Access ad Closure: *American Heart Association Journal*

Transradial Arterial Access for Coronary and Peripheral Procedures; *Executive Summary by the Transradial Committee of the SCAI*

Routine vascular ultrasound after radial artery cauterization detects clinically silent access site complications: Prospective registry of 425 consecutive patients; University of Leipzig, Herzzentrum Ambulation 1 Hour after diagnostic cardiac catheterization, a prospective study of 1009 patients; *Mayo Clinic,* 2006

Radial versus femoral access for coronary angioplasty or intervention and the impact on major bleeding and ischemic events, a systemic review and meta analysis of randomized trials; *American Heart Journal* 2009

Transradial vs transfemoral approach for coronary angiography interventions for patients above 75 years of age; *Catheter Cardiovascular interventions* 2008

Transradial access compared with femoral puncture closure devices in percutaneous coronary procedures; *International Journal of Cardiology,* 2009

BRIEF DESCRIPTION

This specification discloses a self-dilating catheter introducer and obturator device. The self-dilating catheter introducer is comprised of a proximal hub with a central orifice and internal seal; the hub also having a purge valve port joined with an extension tube and external purge valve, joined to and extending distally and longitudinally from the hub is a multi-layer lumen configuration with an overmold compliance coating/sheath with properties of elasticity. Preferably the lumen is formed of two tubular shaped and longitudinally extending layers which are covered with an external layer of compliance/elastomeric material. The inner and middle layers of the lumen are capable of radial expansion when the obturator is proximally inserted while the outer layer of compliance/elastomeric material accommodates this expansion due to its expansion properties. The obturator comprised of female luer fitting compliant to ISO 594-1 and -2, a pliable tube with tapered tip and extending distally is joined to the fitting. The disclosure also relates to a method of using a catheter introducer where the catheter introducer is inserted through an incision and positioned in the body of a patient such that its proximal end is accessible to a medical professional and its distal end is positioned to allow a medical device to be inserted at a desired location in the patient. Additionally the lumen of the catheter introducer may be expanded from a first inner diameter to a second inner diameter by insertion of the desired obturator allowing for an instrument for diagnostic or for deploying an implantable medical device e.g. stent into a body lumen.

The present invention relates generally to medical devices and, in particular, to a self-dilating catheter introducer and obturator system for introducing implantable medical devices into a body cavity. Depending on the size of the orifice or opening in which the device is required to pass through determines the French scale size of the device (e.g. The French scale is a measure of the external diameter of a catheter not internal channel).

In one embodiment, the invention utilizes a dual lumen configuration with an overmold compliance coating/sheath with properties of elasticity, one lumen inserted internally in and joined to the other with each lumen being split longitudinally along the central axis; the splits of each lumen are positioned opposite each other yielding a closed circumference.

In another embodiment, the invention utilizes a single lumen configuration with an overmolded compliance coating/sheath with properties of elasticity, the lumen wall having a fluted profile extending longitudinally and radially around the circumference and length of the lumen.

In yet another embodiment, the invention utilizes a plurality of identical interdigitating/overlapping fingers/leafs/blades joined radially about a central axis and extending longitudinally along the central axis with an overmold compliance coating/sheath with properties of elasticity.

In yet another embodiment, the invention utilizes, a self-dilating catheter comprised of a proximal access fitting with a central orifice and internal seal, joined to and extending distally and longitudinally from the fitting is a multi-layer lumen configuration with an overmold compliance coating/sheath with properties of elasticity.

In all afore mentioned embodiments the device has the capability of accommodating varying French scale lumens/catheters.

BRIEF DESCRIPTION OF THE DRAWINGS

The invention may be better understood and appreciated by reference to the detailed description of specific embodiments presented herein in conjunction with the accompanying drawings of which.

DETAILED DESCRIPTION

While this invention may be embodied in many different forms, there are described in detail herein specific preferred embodiments of the invention. This description is an exemplification of the principles of the invention and is not intended to limit the invention to the particular embodiments illustrated.

Before any embodiments of the invention are explained in detail, it is to be understood that the invention is not limited in its application to the details of the structure and function set forth in the following description or illustrated in the appended drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. "Comprising" also encompasses the terms "consisting of" and "consisting essentially of." The use of "consisting essentially of" means, e.g., that a method may include additional steps, but only if the additional steps do not materially alter the basic and novel characteristics of the claimed method. Unless specified or limited otherwise, the terms "mate", "mated", "joined", "mounted," "connected," "supported," and "coupled" and variations thereof herein are used broadly and encompass both direct and indirect mountings, connections, supports, and couplings. Further, "connected" and "coupled" are not restricted to physical or mechanical connections or couplings. The use of "compliance" the ability of an object to yield elastically when a force is applied "flexibility" (Merriam-Webster). The use of "overmold" is the process of molding over an insert, which becomes integral to the part on cooling.

No admission is made that any reference, including any patent or patent document, cited in this specification constitutes prior art. In particular, it will be understood that unless otherwise stated, reference to any document herein does not constitute an admission that any of these documents forms part of the common general knowledge in the art in the United States or in any other country. Any discussion of the references states what the author asserts and the applicant reserves the right to challenge the accuracy and pertinence of any of the documents cited herein.

As used in this specification and the appended claims, the singular forms "a," "an," and "the" include plural referents unless the content clearly dictates otherwise. As used in this specification and the appended claims, the term "or" is generally employed in its sense including "and/or" unless the content clearly dictates otherwise.

Unless otherwise noted, technical terms are used according to conventional usage. However, as used herein, the following definitions may be useful in aiding the skilled practitioner in understanding the invention. Such definitions shall be applied, unless a different definition is given in the claims or elsewhere in this specification.

In view of the foregoing disadvantages inherent in conventional introducer systems, the invention provides a novel system and method for introduction of intravascular devices.

The full advantage of the Self-dilating Catheter Introducer and Obturator Device in accordance with the invention is realized when optimal French scale deployment size and ergonomically simplified functionality combine to result in a superior system. Thus these capabilities allows for the intravascular procedure to be accomplished as effectively as possible while minimizing the challenging issues communally associated with the current introducer systems.

Reference is now made to FIGS. 1-10 in which a Self-dilating Catheter introducer and Obturator Device, generally designated by reference numeral 10, in accordance with the invention is shown. Device 10 with split lumen embodiment comprises a dilating obturator 30 with female luer fitting 31 and a introducer 20 with joined proximal hub 21, the hub side port 21c joined in the distal area with an extension tube 41 having a joined purge valve 40 on opposite end of extension tube 41.

Figure 1:
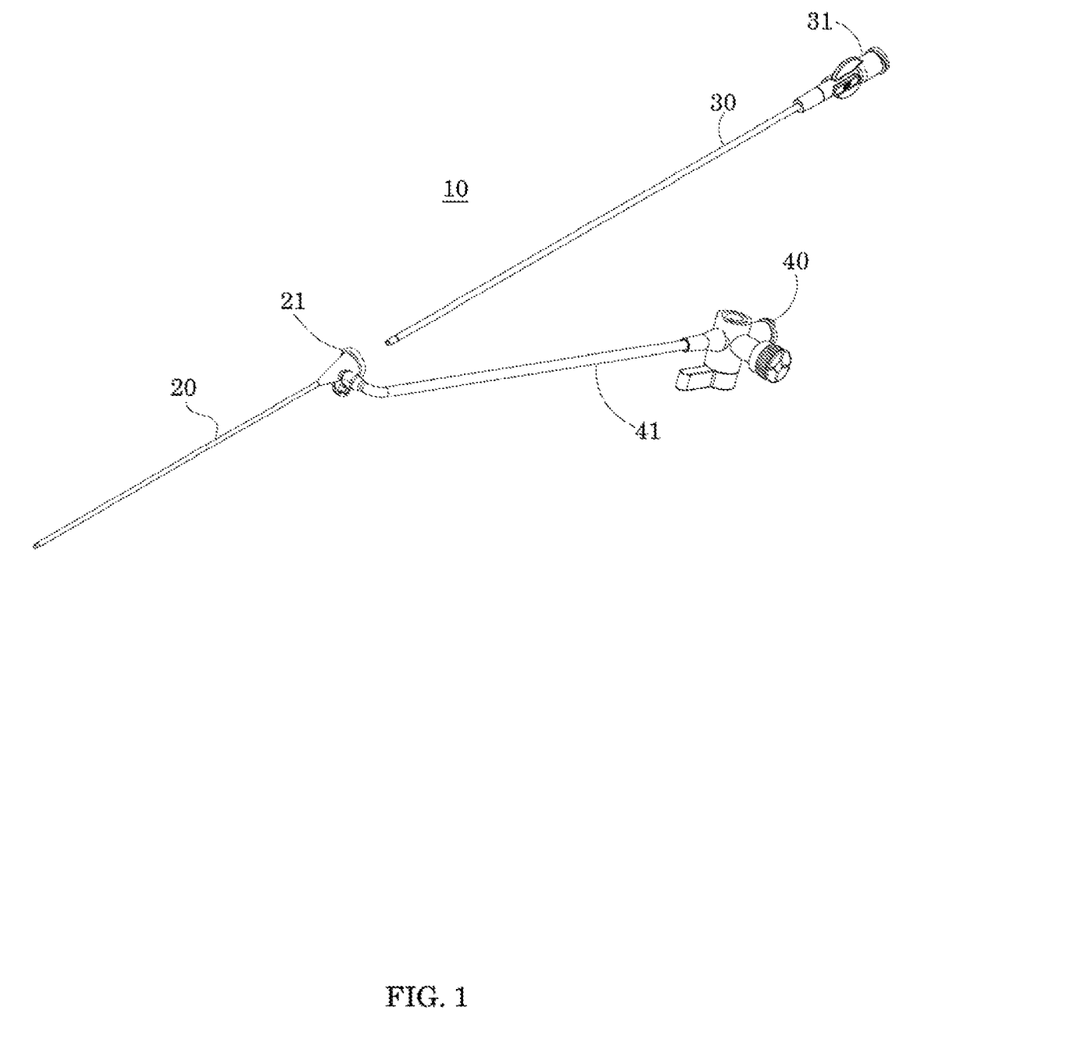
FIG. 1 is an isometric view of the self-dilating introducer with purge valve and obturator, device, all in accordance with the invention.
Figure 2:
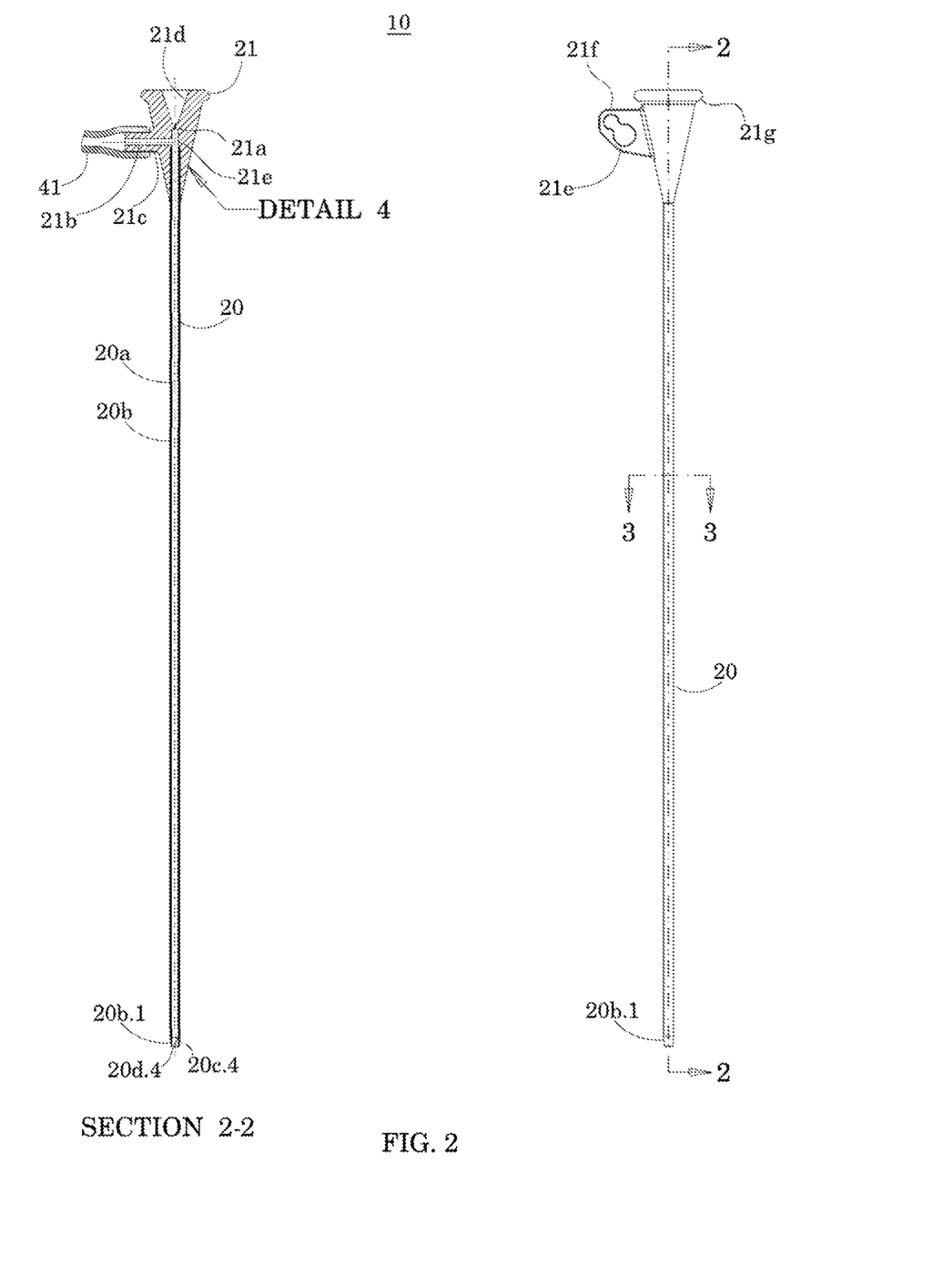
FIG. 2 is a side plan and cross section view of the, self-dilating introducer device, all in accordance with the invention.
Figure 3:
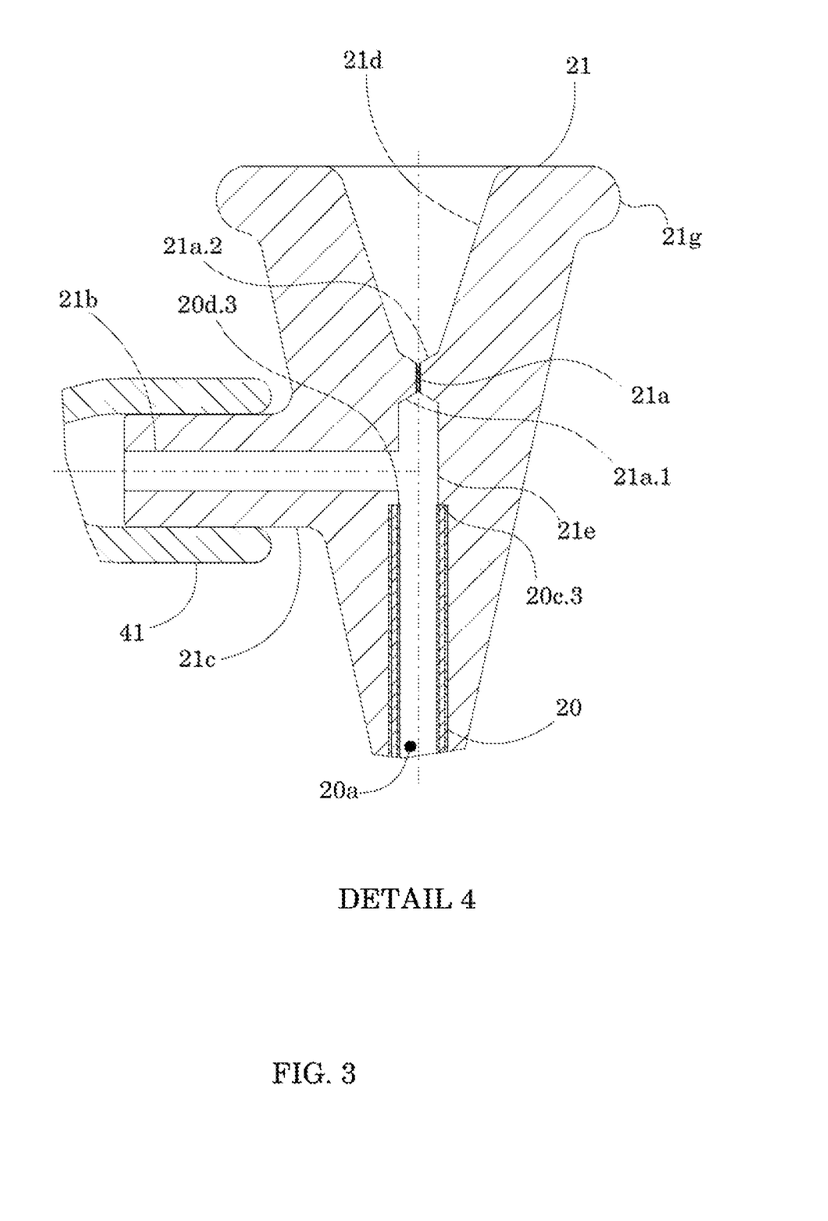
FIG. 3 is a scaled up partial detail view of the proximal hub area of cross section 2-2 in FIG. 2, all in accordance with the invention.
Figure 4:
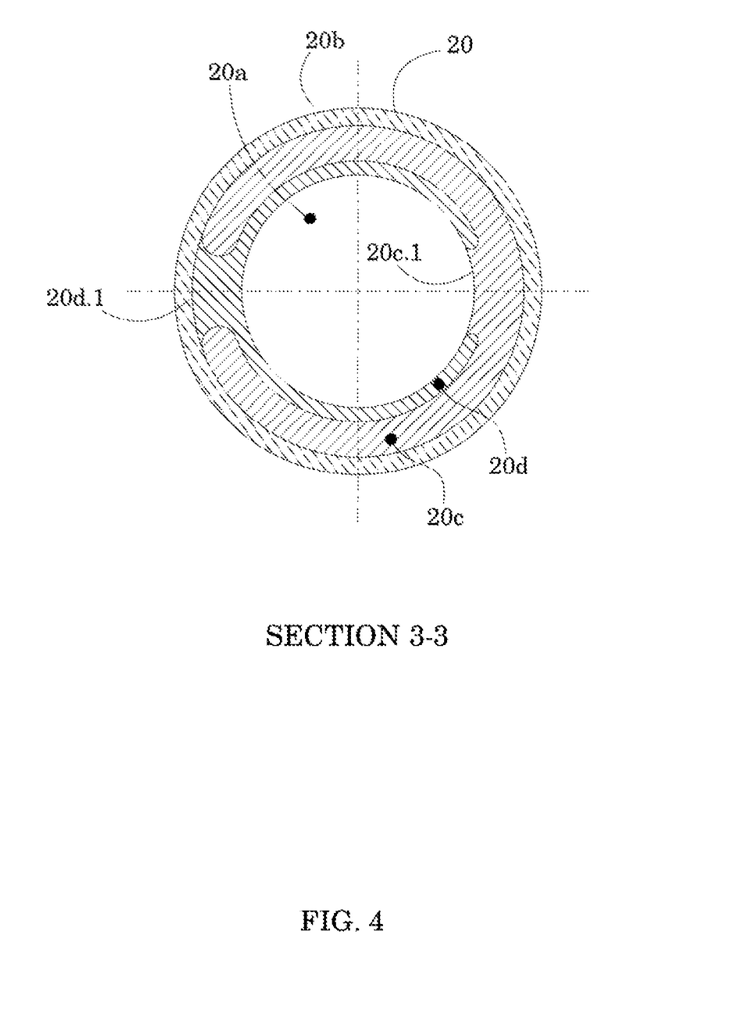
FIG. 4 is a scaled up cross section view of the lumen profile of side view in FIG. 2, all in accordance with the invention.
Figure 5:
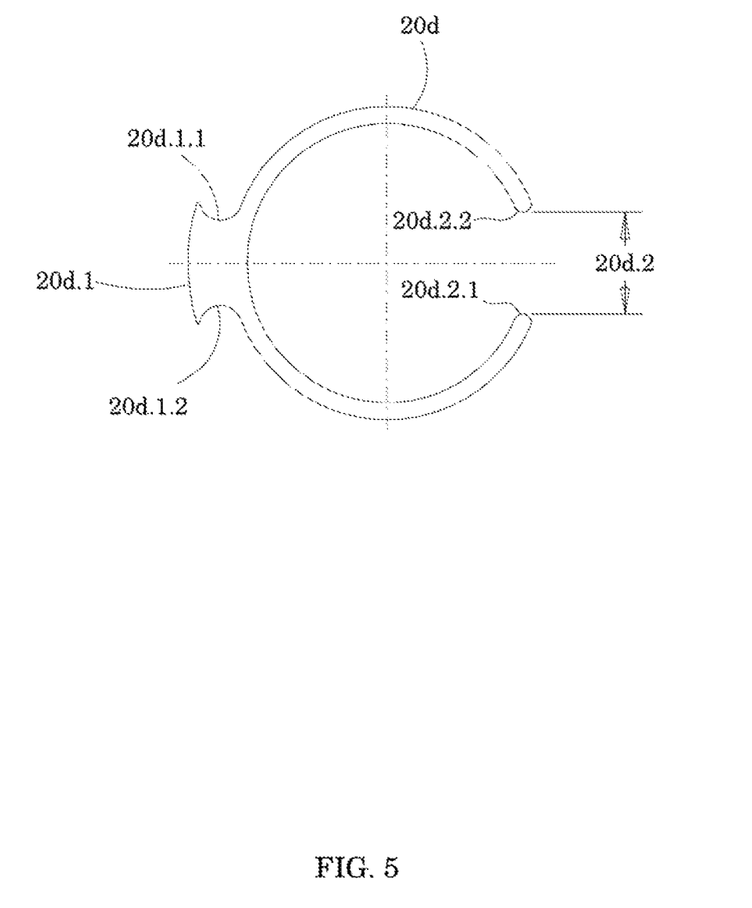
FIG. 5 is a front plan view of the inner lumen profile, all in accordance with the invention.
Figure 6:
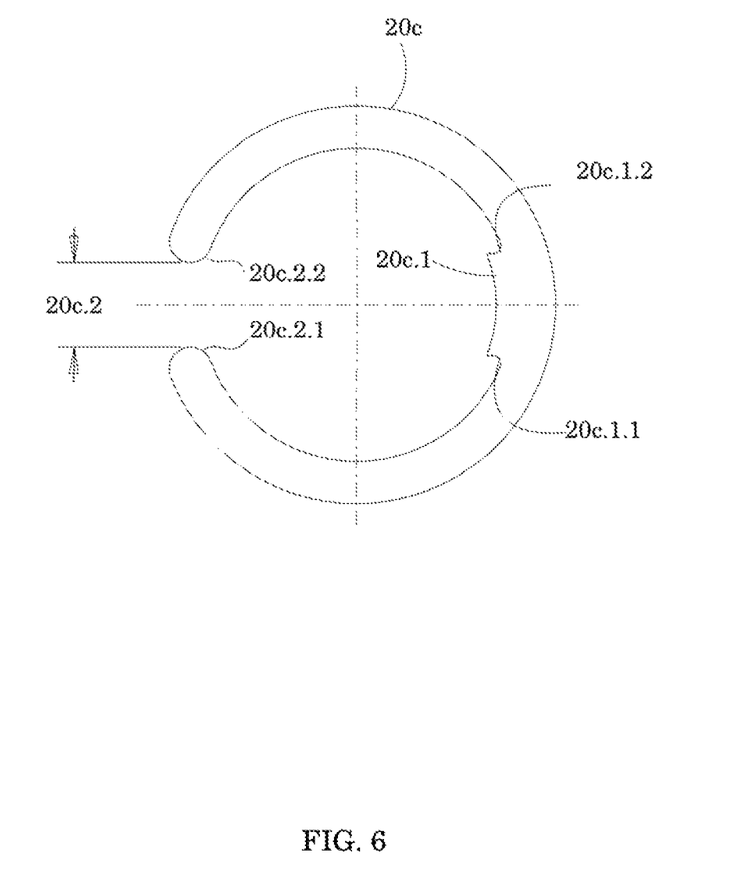
FIG. 6 is a front plan view of the outer lumen profile, all in accordance with the invention.
Figure 7:
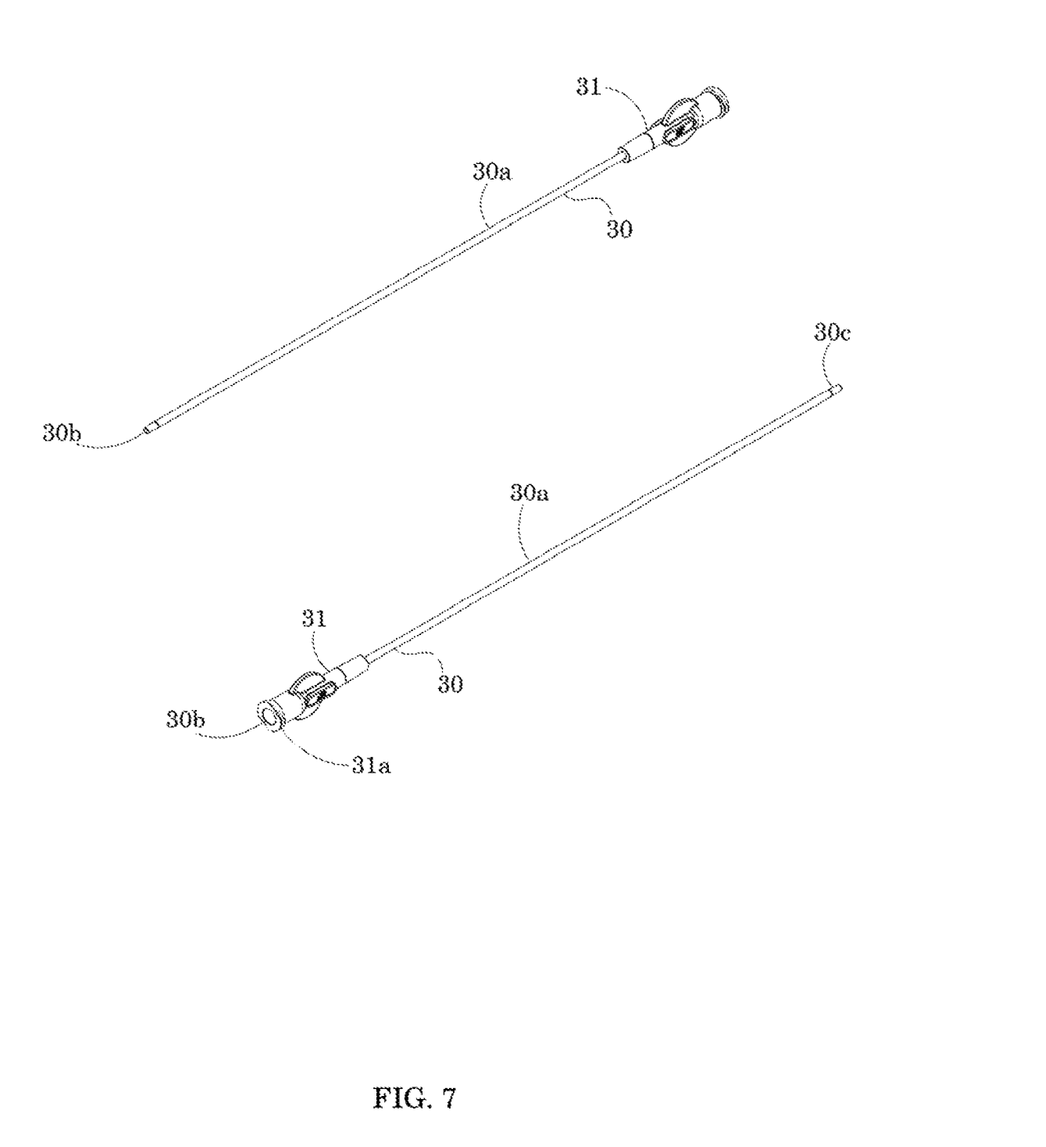
FIG. 7 is an isometric view of the distal and proximal perspective of the obturator, all in accordance with the invention.

Illustrated in FIG. 7 the obturator 30 has a flexible French scale lumen 30a extending distally from the female luer fitting 31 and terminating with a tapered tip 30c, the lumen 30a has a central orifice 30b which traverses along the longitudinal centerline and joins to the tapered internal aperture 31b of the female luer fitting resulting in an unobstructed channel for passage of fluids or devices e.g. saline solution or catheters or guidewires, the set of threads 31a and the tapered internal aperture 31b of the female luer fitting all compliant with ISO 594-1 and -2 standard for 6% taper luer fittings the female luer 31 provides a connection fitting for auxiliary devices e.g. syringe. The obturator can be made from any suitable biocompatible materials e.g. plastics or metals (e.g. nitinol, spring steel).

Illustrated in FIGS. 2, 3, 4, 5, and 6 the introducer 20 comprised of dual split lumen configuration having a mated and joined inner lumen 20d and outer lumen 20c and mated to an external compliance coating/sheath 201 which exhibits elastic properties, the dual split lumens and external compliance coating/sheath extending, distally from and including the hub 21 and terminating with a tapered tip 20b.1, the dual split lumen configuration 20 has it central orifice 20a which traverses from the distal tip along the longitudinal centerline and joins with the hub in an area distally of the hub integrated static seal 21a aligning to the internal aperture 21e of the hub which extends to the distal surface 21a.1 of the integrated static seal 21a resulting in an unobstructed closed channel for passage of fluids through the purge channel 21b then traversing through the extension tube 41 joined to the hub purge port 21c allowing passage to the purge valve 40 providing for the purging of the system e.g. air. Positioned on the most proximal end of the hub 21 a perimeter flange 21g for gripping and a tapered orifice 21d terminating at the proximal surface 21a.2 of the integrated static seal 21a allows for insertion of the obturator 30. A tab 21f extends outbound from the hub surface and with an orifice 21e for anchoring the introducer in position as required. Additionally illustrated the mating of the inner lumen 20d and outer lumen 20c joined to the external compliance coating/sheath 20b. The inner lumen 20d illustrated in FIG. 5 with a split 20d.2 with equally spaced ends 20d.2.1 and 20d.2.2 about the longitudinal centerline and extending longitudinally from the most distal edge 20d.4 to the most proximal edge 20d.3, a rail 20d.1 positioned opposite the split and facing outbound with equally spaced recessed channels 20d.1.1 and 20d.1.2 about the longitudinal centerline and extending longitudinally from the most distal edge 20d.4 to the most proximal edge 20d3. The outer lumen 20c Illustrated in FIG. 6 with a split 20c2 with equally spaced ends 20c.2.1 and 20c.2.2 about the longitudinal centerline and extending longitudinally from the most distal edge 20e.4 to the most proximal edge 20c3, a rail 20c.1 positioned opposite the split and facing inbound with equally spaced recessed channels 20c.1.1 and 20c.1.2 about the longitudinal centerline and extending longitudinally from the most distal edge 20c.4 to the most proximal edge 20c3. The split end surfaces 20d.2.1 and 20d.2.2 of the inner lumen 20d join with the recessed channels 20c.1.1 and 20c.1.2 respectively of the outer lumen 20c, the split end surfaces 20c.2.1 and 20c.2.2 of the outer lumen 20c join with the recessed channels 20d.1.1 and 20d1.2 respectively of the inner lumen 20d. This lumen configuration allows the lumen orifice 20a to dilate/expand when the obturator 30 of the desired. French scale is inserted the configuration allows the orifice 20a to return to its normal state when the obturator 30 is removed. The introducer can be made from any single and/or combination of suitable biocompatible materials e.g. plastics or metals, and compliance materials.

Figure 8:
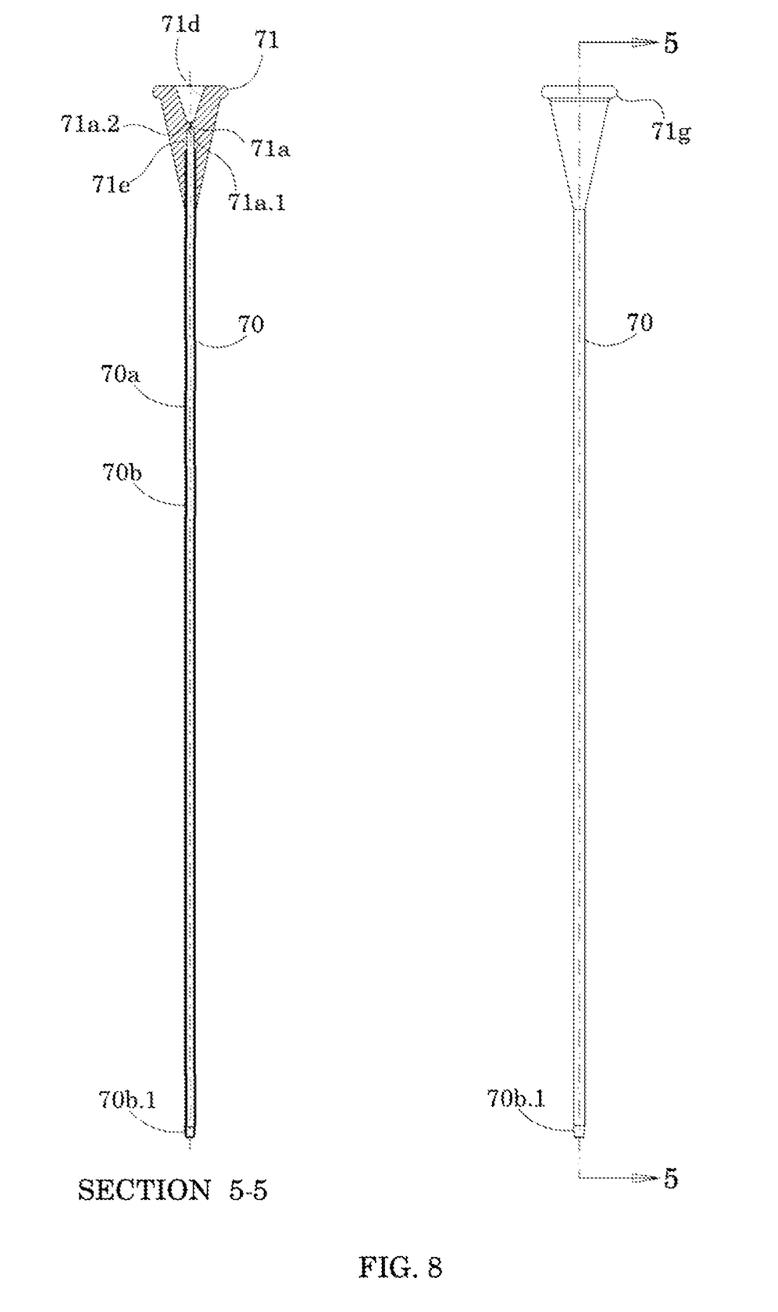
FIG. 8 is a side plan and cross section view of the, self-dilating introducer, non-purge valve device embodiment, all in accordance with the invention.

As presented in this specification reference is now made to FIG. 8 in which another embodiment of the introducer 70 wherein the hub side port and anchor tab have been omitted, the introducer 70 comprised of dual split lumen configuration having to mated and joined inner lumen 70d and outer lumen 70c and mated to an external compliance coating/sheath 70b which exhibits elastic properties the dual split lumens and external compliance coating/sheath extending distally from a hub 71 and terminating with a tapered tip 70b.1, the dual split lumen configuration 70 has a central orifice 70a which traverses front the distal tip along the longitudinal centerline and joins with the hub in an area distally of the hub integrated static seal 71a aligning to the internal aperture 71e of the hub which extends to the distal surface 71a.1 of the static seal 71a. Positioned on the most proximal end of the hub 71 a perimeter flange 71g for gripping and a tapered orifice 71d terminating at the proximal surface 71a.2 of the static seal 71a allows for insertion of the obturator 30.

Figure 9:
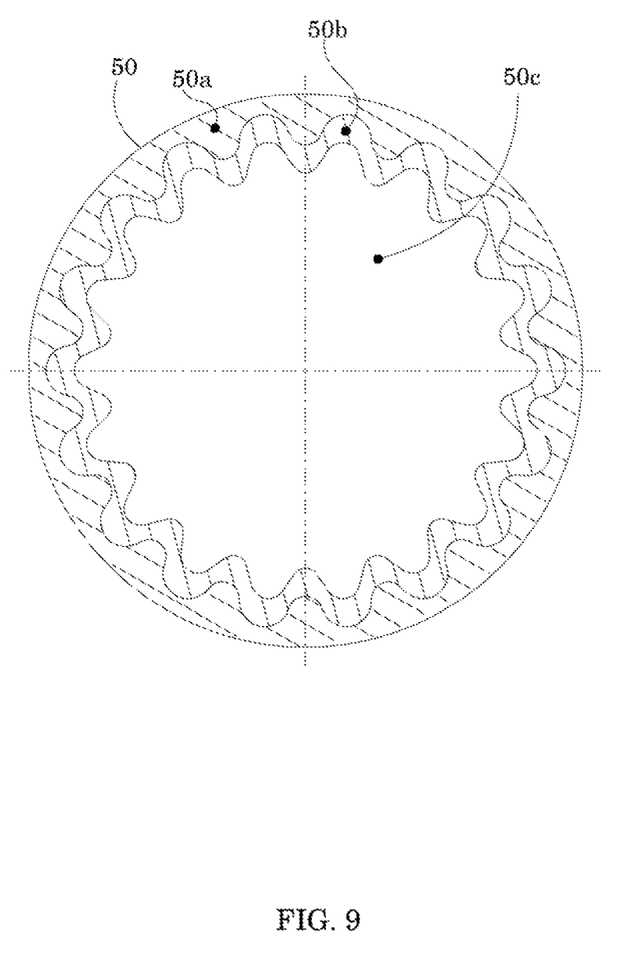
FIG. 9 is a front plan view of the fluted lumen profile embodiment, all in accordance with the invention.

As presented in this specification reference is now made to FIG. 9 in which yet another embodiment wherein the lumen of the introducer 20 is comprised of a single lumen 50 with a wave pattern profile configuration having an inner lumen 50b and mated to an external compliance coating/sheath 50a which exhibits elastic properties, the single lumen and external compliance coating/sheath extending distally from a hub 21 and terminating with a tapered tip 20b.1, the single lumen configuration 50 has a central orifice 50c which traverses from the distal tip along the longitudinal centerline and joins with the hub in an area distally of the hub static seal 21a aligning to the internal aperture 21e of the hub which extends to the distal surface 21a.1 of the static seal 21a resulting in an unobstructed closed channel. This lumen configuration allows the lumen orifice 50c to dilate/expand when the obturator 30 of the desired French scale is inserted; the configuration allows the orifice 50c to return to its normal state when the obturator 30 is removed.

Figure 10:
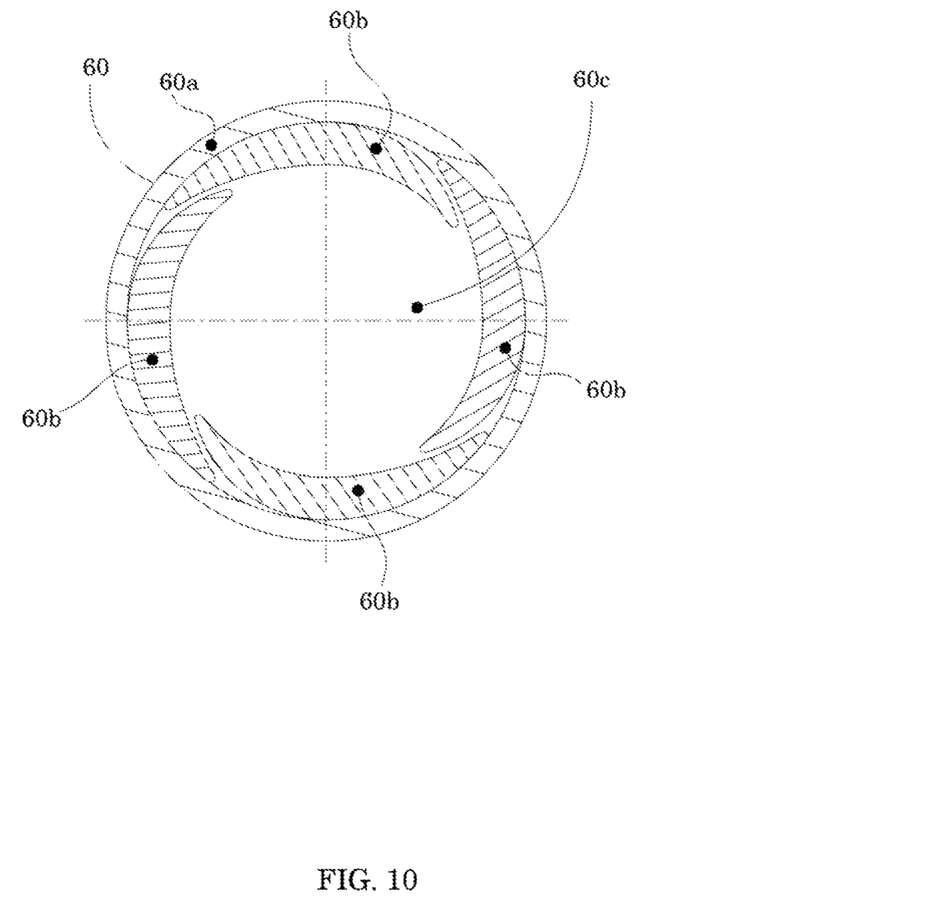
FIG. 10 is as front plan view of the identical interdigitating/overlapping fingers/leafs/blades lumen profile embodiment, all in accordance with the invention.

As presented in this specification reference is now made to FIG. 10 in which yet another embodiment wherein the lumen of the introducer 20 is comprised of identical interdigitating/overlapping fingers/leafs/blades resulting in a multi-layer lumen 60 with an interdigitating/overlapping radial pattern profile configuration having an inner multi-layer lumen 60b and mated to an external compliance coating/sheath 60a which exhibits elastic properties, the multi-layer lumen and external compliance coating/sheath extending distally from as hub 21 and terminating with a tapered tip 20b.1, the multi-layer lumen configuration 60 has a central orifice 60c which traverses from the distal tip along the longitudinal centerline and joins with the hub in an area distally of the hub static seal 21a aligning to the internal aperture 21e of the hub which extends to the distal surface 21a.1 of the static seal 21a resulting in an unobstructed closed channel. This lumen configuration allows the lumen orifice 60c to dilate/expand when the obturator 30 of the desired French scale is inserted; the configuration allows the orifice 60c to return to its normal state when the obturator 30 is removed.

As presented in this specification the method of use for but not limited to a Vascular Access procedure. Once a local anesthesia has been administered make an incision using a 21g needle, then insert a angiographic guidewire and advance to desired location, check the position with fluoroscopy once in position remove the needle and insert the sheath introducer over the guidewire. Once introducer is in position insert the appropriate French scale obturator and complete the procedure.

The foregoing description is considered as illustrative only of the principles of the invention. Further, since numerous modifications and changes may readily occur e.g. tapered or multiple split lumen etc., to those skilled in the art, it is not desired to limit the invention to the exact construction and operation shown and described, and accordingly, all suitable modifications and equivalents are considered to fall within the scope of the invention. Various features and advantages of the invention are set forth in the following claims.

All publications, patents and patent applications referenced in this specification are indicative of the level of ordinary skill in the art to which this invention pertains. All publications, patents and patent applications are herein expressly incorporated by reference to the same extent as if each individual publication or patent application was specifically and individually indicated by reference. In case of conflict between the present disclosure and the incorporated patents, publications and references, the present disclosure should control.

The invention claimed is:

1. A self-dilating introducer system for vascular access into the human vascular system comprising:
a self-dilating introducer having a wall with an inner lumen layer, an outer lumen layer, and an external compliance coating/sheath molded over the inner and outer lumen layers, the inner lumen layer having a split with spaced ends, a rail positioned opposite the split and facing outbound with recessed channels, the outer lumen layer having a split with spaced ends, a rail positioned opposite the split and facing inbound with recessed channels, and wherein the ends of the inner lumen layer are configured to join with the recessed channels of the outer lumen and the ends of the outer lumen layer are configured to join with the recessed channels of the inner lumen;
a hub with integrated seal and side port joined to the self-dilating introducer and having a distal end, a proximal end and a central orifice extending from the proximal end of the hub to the distal end of the hub along a central longitudinal centerline;
a side port having a distal end, a proximal end and a central orifice, the side port being in communication with the central orifice of the hub;
a extension tube being joined to the distal end of the side port;
a purge valve being joined to the extension tube;
a dilating obturator with a flexible tubular body joined proximally to a luer fitting, the obturator has a distal end with a tapered distal tip, a proximal end and a central orifice extending between the proximal end of the obturator and the distal end of the obturator; and wherein the inner and outer lumen layers are configured to automatically radially expand when the dilating obturator is inserted through the self-dilating introducer and automatically contract when the dilating obturator is removed from the self-dilating introducer.

2. The self-dilating introducer system of claim 1, wherein the hub with integrated seal is of a compliance material.

3. The self-dilating introducer system of claim 1, wherein the hub further comprises a perimeter flange for allowing gripping.

4. The self-dilating introducer system of claim 1, wherein the hub further comprises a tab with orifice for allowing the introducer to be anchored.

5. The self-dilating introducer system of claim 1, wherein the hub further comprises a proximal tapered orifice for allowing device insertion.

6. A self-dilating introducer system for vascular access into the human vascular system comprising:

a self-dilating introducer having a wall with an inner lumen layer, an outer lumen layer, and an external compliance coating/sheath molded over the inner and outer lumen layers, the inner lumen layer having a split with spaced ends, a rail positioned opposite the split and facing outbound with recessed channels, the outer lumen layer having a split with spaced ends, a rail positioned opposite the split and facing inbound with recessed channels, and wherein the ends of the inner lumen layer are configured to join with the recessed channels of the outer lumen and the ends of the outer lumen layer are configured to join with the recessed channels of the inner lumen;

a hub with integrated seal and side port joined to the self-dilating introducer and having a distal end, a proximal end and a central orifice extending from the proximal end of the hub to the distal end of the hub along a central longitudinal centerline;

a dilating obturator with a flexible tubular body joined proximally to a luer fitting, the obturator has a distal end with a tapered distal tip, a proximal end and a central orifice extending between the proximal end of the obturator and the distal end of the obturator; and wherein the inner and outer lumen layers are configured to automatically radially expand when the dilating obturator is inserted through the self-dilating introducer and automatically return to a radially unexpanded state when the dilating obturator is removed from the self-dilating introducer.

7. The self-dilating introducer system of claim 6, wherein the hub with integrated seal is of a compliance material.

8. The self-dilating introducer system of claim 6, wherein the hub further comprises a perimeter flange for allowing gripping.

9. The self-dilating introducer system of claim 6, wherein the hub further comprises a tab with orifice for allowing the introducer to be anchored.

10. The self-dilating introducer system of claim 6, wherein the hub further comprises a proximal tapered orifice for allowing device insertion.

* * * * *